United States Patent
Fagan et al.

(10) Patent No.: US 12,310,615 B2
(45) Date of Patent: May 27, 2025

(54) ARTICULATING ULTRASONIC SURGICAL INSTRUMENTS AND SYSTEMS

(71) Applicant: Covidien LP, Mansfield, MA (US)

(72) Inventors: James R. Fagan, Erie, CO (US); Thomas E. Drochner, Longmont, CO (US); Michael B. Lyons, Boulder, CO (US); David J. Van Tol, Boulder, CO (US); Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 307 days.

(21) Appl. No.: 17/797,175

(22) PCT Filed: Mar. 2, 2021

(86) PCT No.: PCT/US2021/020473
§ 371 (c)(1),
(2) Date: Aug. 3, 2022

(87) PCT Pub. No.: WO2021/202035
PCT Pub. Date: Oct. 7, 2021

(65) Prior Publication Data
US 2023/0053012 A1    Feb. 16, 2023

Related U.S. Application Data

(60) Provisional application No. 63/003,985, filed on Apr. 2, 2020.

(51) Int. Cl.
*A61B 17/32* (2006.01)
*A61B 34/37* (2016.01)
(Continued)

(52) U.S. Cl.
CPC ...... *A61B 17/320092* (2013.01); *A61B 34/37* (2016.02); *A61B 2017/00402* (2013.01);
(Continued)

(58) Field of Classification Search
CPC .. A61B 17/320092; A61B 2017/00402; A61B 2017/2927; A61B 2017/320071;
(Continued)

(56) References Cited

U.S. PATENT DOCUMENTS

| 10,413,316 B2 * | 9/2019 | Lyons | ............ A61B 17/320092 |
| 11,337,717 B2 * | 5/2022 | Lyons | ................ A61B 17/2909 |

(Continued)

FOREIGN PATENT DOCUMENTS

| EP | 0592243 A2 | 4/1994 |
| EP | 3170462 A1 | 5/2017 |
| WO | 9952489 A1 | 10/1999 |

OTHER PUBLICATIONS

Communication Pursuant to Article 94(3) EPC issued in corresponding European Application No. 21 713 855.1 dated Apr. 26, 2024, 5 pages.

(Continued)

Primary Examiner — Julian W Woo

(57) ABSTRACT

An articulating ultrasonic surgical end effector for use with a hand-held surgical instrument or a robotic surgical system includes an articulation assembly, a clevis operably coupled to the articulation assembly, and a transducer assembly pivotably coupled to the clevis. The transducer assembly includes a transducer housing and an ultrasonic transducer and a waveguide disposed within the transducer housing. The waveguide is coupled to the ultrasonic transducer and extends distally from the ultrasonic transducer. The transducer assembly also includes an ultrasonic blade disposed at the distal end of the waveguide and extending from the transducer housing and a clamp arm pivotably coupled to the transducer housing and movable relative to the ultrasonic blade between an open position and a clamping position. Ultrasonic energy produced by the ultrasonic transducer is (Continued)

transmitted along the waveguide to the ultrasonic blade for treating tissue.

20 Claims, 7 Drawing Sheets

(51) Int. Cl.
*A61B 17/00* (2006.01)
*A61B 17/29* (2006.01)

(52) U.S. Cl.
CPC ................ *A61B 2017/2927* (2013.01); *A61B 2017/320071* (2017.08); *A61B 2017/320075* (2017.08); *A61B 2017/320094* (2017.08); *A61B 2017/320098* (2017.08)

(58) Field of Classification Search
CPC ....... A61B 2017/320075; A61B 2017/320094; A61B 2017/2926
See application file for complete search history.

(56) References Cited

U.S. PATENT DOCUMENTS

2014/0005702 A1    1/2014  Timm et al.
2024/0268853 A1*  8/2024  Stulen ............ A61B 17/320092

OTHER PUBLICATIONS

International Search Report and Written Opinion of the International Searching Authority issued in corresponding application PCT/US2021/020473 mailed Jun. 16, 2021 (10 pages).

* cited by examiner

ARTICULATING ULTRASONIC SURGICAL INSTRUMENTS AND SYSTEMS

CROSS REFERENCE TO RELATED APPLICATIONS

This application is a U.S. National Stage Application filed under 35 U.S.C. § 371(a) of International Patent Application No. PCT/US2021/020473, filed Mar. 2, 2021, which claims the benefit of the filing date of provisional U.S. Patent Application No. 63/003,985, filed on Apr. 2, 2020.

FIELD

The present disclosure relates to surgical instruments and systems and, more particularly, to articulating ultrasonic surgical instruments and systems including distally-located ultrasonic transducers.

BACKGROUND

Ultrasonic surgical instruments and systems utilize ultrasonic energy, i.e., ultrasonic vibrations, to treat tissue. More specifically, a typical ultrasonic surgical instrument or system includes a transducer configured to produce and transmit mechanical vibration energy at ultrasonic frequencies along a waveguide to an ultrasonic end effector configured to treat tissue, e.g., coagulate, cauterize, fuse, seal, cut, desiccate, fulgurate, or otherwise treat tissue. Traditionally, the transducer remains external of the surgical site, while the waveguide extends from the transducer into the surgical site to provide the ultrasonic energy to the ultrasonic end effector. The ultrasonic end effector is manipulated into position to treat a desired tissue or tissues.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

As used herein, the term "distal" refers to the portion that is being described which is further from a user, while the term "proximal" refers to the portion that is being described which is closer to a user. Further, to the extent consistent, any or all of the features of any of the devices detailed herein may be used in conjunction with any or all of the other devices detailed herein.

In accordance with aspects of the present disclosure, an articulating ultrasonic surgical end effector is provided. The end effector includes an articulation assembly, a clevis operably coupled to the articulation assembly, and a transducer assembly pivotably coupled to the clevis. The transducer assembly includes a transducer housing, and an ultrasonic transducer and a waveguide disposed within the transducer housing. The waveguide is operably coupled to the ultrasonic transducer and extends distally from the ultrasonic transducer. The transducer assembly also includes an ultrasonic blade and a clamp arm. The ultrasonic blade is disposed at the distal end of the waveguide, and extending from the transducer housing. The clamp arm is pivotably coupled to the transducer housing and movable relative to the ultrasonic blade between an open position and a clamping position. Ultrasonic energy produced by the ultrasonic transducer is transmitted along the waveguide to the ultrasonic blade for treating tissue.

In aspects of the present disclosure, a pulley and cable arrangement operably couples the transducer assembly to the clevis to permit pivoting of the transducer assembly relative to the clevis.

In aspects of the present disclosure, a pulley and cable arrangement extends between the clamp arm and the clevis to permit pivoting of the clamp arm relative to the ultrasonic blade regardless of an articulated position of the transducer assembly relative to the clevis.

In aspects of the present disclosure, the end effector further includes a pulley gear rotatably coupled to a proximal portion of the clevis, a distal gear rotatably coupled to a distal portion of the clevis and operably coupled to the transducer assembly such that rotation of the distal gear pivots the transducer assembly relative to the clevis, and a driver, belt, or chain coupling the pulley gear to the distal gear. The end effector may further include a first cable and a second cable operably coupled to the pulley gear. The first cable and the second cable may be configured to rotate the pulley gear to cause the transducer assembly to pivot relative to the clevis when one of the first cable or the second cable is proximally actuated, and articulate a distal articulation link of the articulation assembly relative to a proximal articulation link of the articulation assembly when both of the first cable and the second cable are proximally actuated.

In aspects of the present disclosure, the ultrasonic transducer includes at least one piezoelectric element and at least one electrode. The ultrasonic transducer, in aspects, defines a circular cross-sectional configuration.

In aspects of the present disclosure, a first notch and a second notch are defined along an outer surface of the ultrasonic transducer, on opposing sides thereof. The ultrasonic transducer may include at least one piezoelectric element operably coupled to the first notch and at least one piezoelectric element operably coupled to the second notch. The piezoelectric elements may be configured to produce ultrasonic vibrations in a torsional or longitudinal direction.

A surgical instrument provided in accordance with aspects of the present disclosure includes a handle assembly having an elongated body portion extending distally therefrom, and an articulating ultrasonic surgical end effector according to any of the above aspects, wherein the articulation assembly thereof extends distally from the elongated body portion of the handle assembly.

A surgical system provided in accordance with aspects of the present disclosure includes a robotic surgical system having a control device, a robotic arm, and an articulating ultrasonic surgical end effector according to any of the above aspects, wherein the articulation assembly extends distally from the robotic arm of the robotic surgical system.

In yet another aspect of the present disclosure, an articulating ultrasonic surgical end effector is provided and includes an articulating section having a plurality of articulating links configured to enable articulation in at least two different directions and a transducer assembly extending distally from the articulating section. The transducer assembly includes a transducer housing, and an ultrasonic transducer and a waveguide disposed within the transducer housing. The waveguide is operably coupled to, and extends distally from, the ultrasonic transducer. The transducer assembly further includes an ultrasonic blade disposed at the distal end of the waveguide and extending from the transducer housing. A clamp arm is pivotably coupled to the transducer housing and movable relative to the ultrasonic blade between an open position and a clamping position.

Ultrasonic energy produced by the ultrasonic transducer is transmitted along the waveguide to the ultrasonic blade for treating tissue.

In aspects of the present disclosure, a plurality of articulation cables is operably coupled to at least one of the plurality of articulating links and configured to articulate the articulating section.

In aspects of the present disclosure, the ultrasonic transducer includes at least one piezoelectric element and at least one electrode.

In aspects of the present disclosure, the ultrasonic transducer defines a circular cross-sectional configuration.

In aspects of the present disclosure, a first notch and a second notch are defined along an outer surface of the ultrasonic transducer, on opposing sides thereof. The ultrasonic transducer may include at least one piezoelectric element operably coupled to the first notch and at least one piezoelectric element operably coupled to the second notch. The piezoelectric elements may be configured to produce ultrasonic vibrations in a torsional or longitudinal direction.

A surgical instrument provided in accordance with aspects of the present disclosure includes a handle assembly having an elongated body portion extending distally therefrom, and an articulating ultrasonic surgical end effector according to any of the above aspects, wherein the articulating section thereof extends distally from the elongated body portion of the handle assembly.

A surgical system provided in accordance with aspects of the present disclosure includes a robotic surgical system having a control device, a robotic arm, and an articulating ultrasonic surgical end effector according to any of the above aspects, wherein the articulation section thereof extends distally from the robotic arm of the robotic surgical system.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

The present disclosure relates to articulating ultrasonic surgical instruments and systems that include distally-located ultrasonic transducers sized to enable use in minimally-invasive surgical procedures and/or other surgical procedures.

In some aspects, the ultrasonic transducer, waveguide, blade, and jaw are pivotable relative to a clevis to enable pitch articulation of the instrument, while a pivoting joint coupling the clevis to the shaft enables yaw articulation. By enabling pivoting of the ultrasonic transducer, waveguide, blade, and jaw relative to the clevis, the jaw and blade are positioned closer to the pivot point which creates less dead space, with the larger components, e.g., the ultrasonic transducer and portions of the waveguide, positioned in a "tail" region on the opposite side of the pivot. A housing enclosing the ultrasonic transducer and portions of the waveguide may include supports to retain the transducer/waveguide assembly at one or more node locations or other suitable location (s). The articulation in these aspects may be accomplished via a belt driven or chain driven configuration, cables, or in any other suitable manner and may be actuated by the rotation of a robotic motor, which may then translate through a series of gears and/or pulleys to cause the desired articulation.

In other aspects, a robotic "knuckle" or "wrist" is utilized. Unlike the aspects described above, the ultrasonic transducer is positioned distally of all of the articulation components. In such aspects, the transducer/waveguide assembly may likewise be mounted at a node, e.g., wherein a housing sandwiches a flange of the waveguide at a node, or other suitable location. In such aspects, the articulation may be accomplished via a cable driven system or other suitable mechanism. Combinations of the above aspects are also contemplated.

Figure 1:
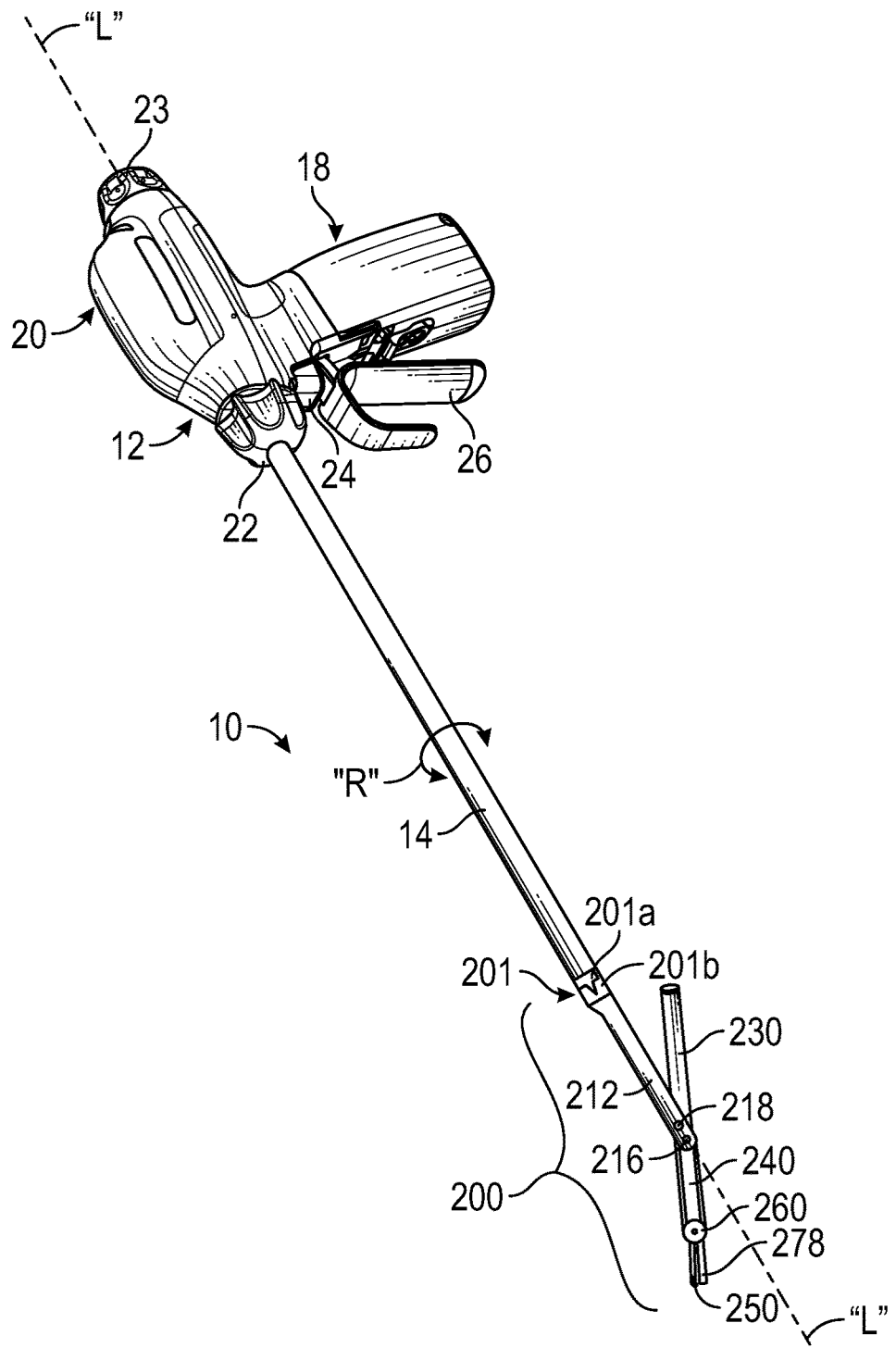
FIG. 1 is a side, perspective view of an endoscopic surgical instrument configured for use in accordance with the aspects and features of present disclosure and including an ultrasonic articulating end effector.

Referring generally to FIG. 1, an endoscopic surgical instrument exemplifying the aspects and features of the present disclosure is shown generally identified by reference numeral 10. For the purposes herein, endoscopic surgical instrument 10 is generally described. Aspects and features of endoscopic surgical instrument 10 not germane to the understanding of the present disclosure are omitted to avoid obscuring the aspects and features of the present disclosure in unnecessary detail.

Endoscopic surgical instrument 10 generally includes a handle assembly 12, an elongated body portion 14, and an articulating ultrasonic surgical end effector 200. Aspects of end effector 200 and its components are described in greater detail below. Handle assembly 12 supports a battery assembly 18 and a generator assembly 20, and includes a first rotation knob 22, a second rotation knob 23, an activation button 24, and a clamp trigger 26.

Clamp trigger 26 of endoscopic surgical instrument 10 is selectively manipulatable to actuate a motor, other powered drive mechanism, or a manual drive mechanism, e.g., gears, pulleys, tension cables, etc., to transition end effector 200 between an open condition and a clamping condition, as detailed below.

First rotation knob 22 is selectively manipulatable, in a first manner, e.g., a rotational manner, to rotate (e.g., roll) elongated body portion 14 and, thus, end effector 200 relative to handle assembly 12 (e.g., around a longitudinal axis "L" defined by elongated body portion 14 in either direction represented by arrow "R"). First rotation knob 22 is selectively manipulatable in a second manner, e.g., a translational manner, to articulate end effector 200 (e.g., yaw articulation) relative to elongated body portion 14 about a pivot axis "P" (FIGS. 3 and 4) in one direction. First rotation knob 22 may be controlled by a manual drive mechanism or by a powered drive mechanism. Second rotation knob 23 is selectively manipulatable, in a first manner, e.g., a rotational manner, to actuate a motor, other powered drive mechanism, or a manual drive mechanism, e.g., gears, pulleys, tension cables, etc., to articulate (e.g., yaw articulation) end effector 200 relative to elongated body portion 14 about pivot axis "P" (FIGS. 3 and 4), and in a second manner, e.g., a translational manner, to pivot (e.g., pitch articulation) components of end effector 200, as detailed below. As an alternative to first and second rotation knobs 22, 23, additional or alternative suitable actuation mechanism(s), e.g., toggle switches, joysticks, buttons, etc., may be provided.

Battery assembly 18 and generator assembly 20 cooperate, upon activation of activation button 24, to supply power to end effector 200 to enable the generation of ultrasonic energy for treating tissue therewith, e.g., to coagulate, cauterize, fuse, seal, cut, desiccate, fulgurate, or otherwise treat tissue, as detailed below. Battery assembly 18 and generator assembly 20 are each releasably secured to handle assembly 12, and are removable therefrom to facilitate disposal of handle assembly 12, with the exception of battery assembly 18 and generator 20. However, it is contemplated that any or all of the components of endoscopic surgical instrument 10 may be configured as disposable single-use components or sterilizable multi-use components, and/or that endoscopic surgical instrument 10 may be connectable to a remote power source or generator rather than having such components on-board.

Figure 2:
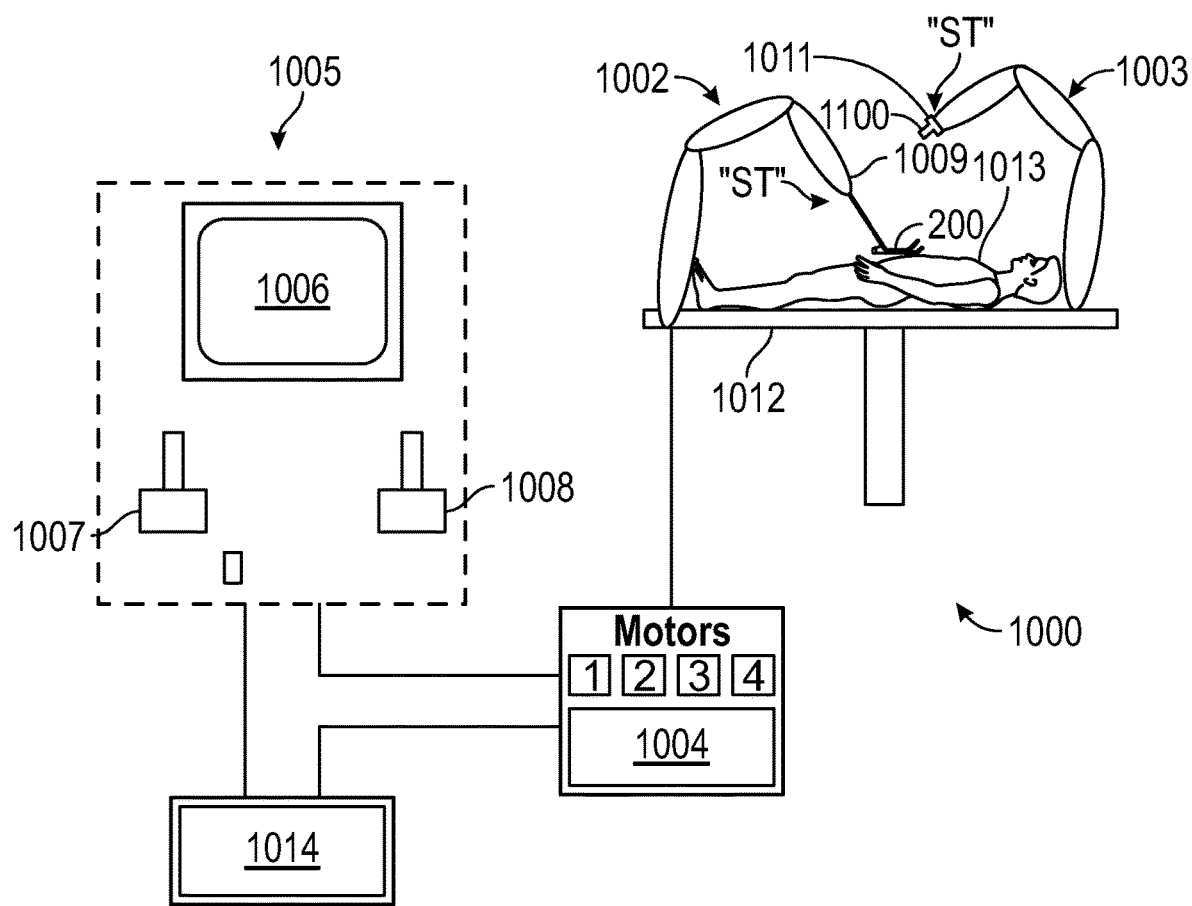
FIG. 2 is a schematic illustration of a robotic surgical system configured for use in accordance with the aspects and features of present disclosure and including an ultrasonic articulating end effector.

Referring generally to FIG. 2, an aspect of a robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 200, 1100. End effector 200, as noted above with respect to endoscopic surgical instrument 10 (FIG. 1), and as described in greater detail below, is an articulating ultrasonic surgical end effector. End effector 1100 may be any other suitable surgical end effector, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" (including end effectors 200, 1100) execute a desired movement and/or function according to a corresponding input from manual input devices 1007, 1008, respectively. Control device 1004 may also be configured in such a way that it regulates the movement of robot arms 1002, 1003 and/or of the motors.

Figure 3:
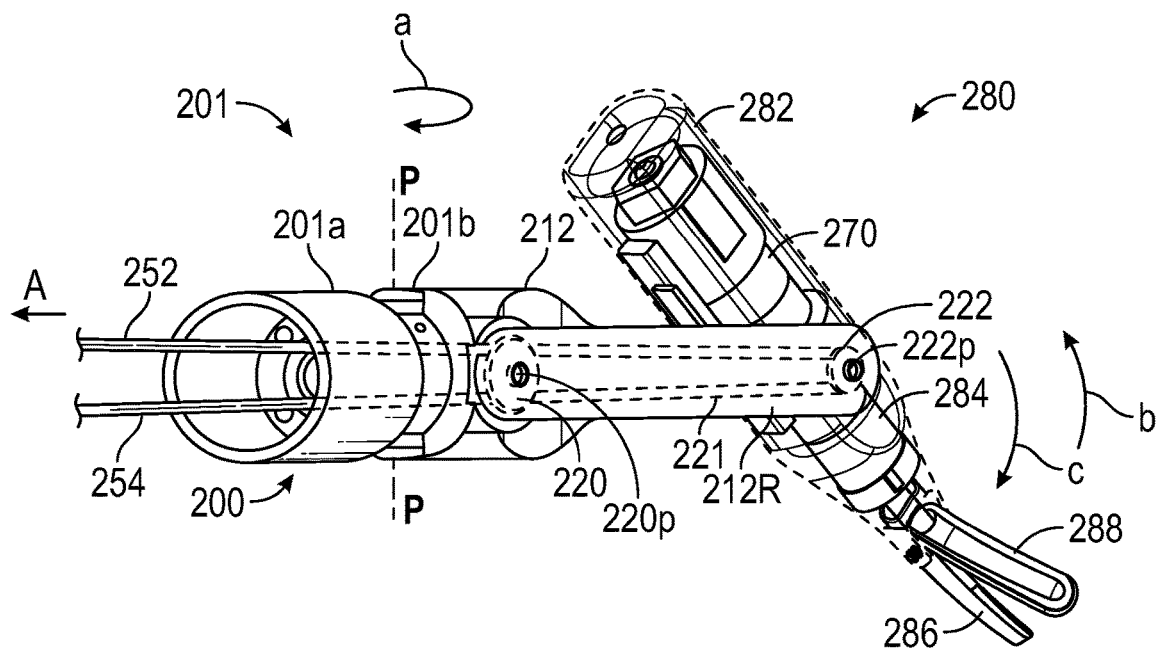
FIG. 3 is an enlarged, side, perspective view of a first side of an ultrasonic articulating end effector pivoted in a first direction in accordance with the present disclosure and configured for use with the endoscopic surgical instrument of FIG. 1, the robotic surgical system of FIG. 2, or any other suitable surgical instrument or system.
Figure 4:
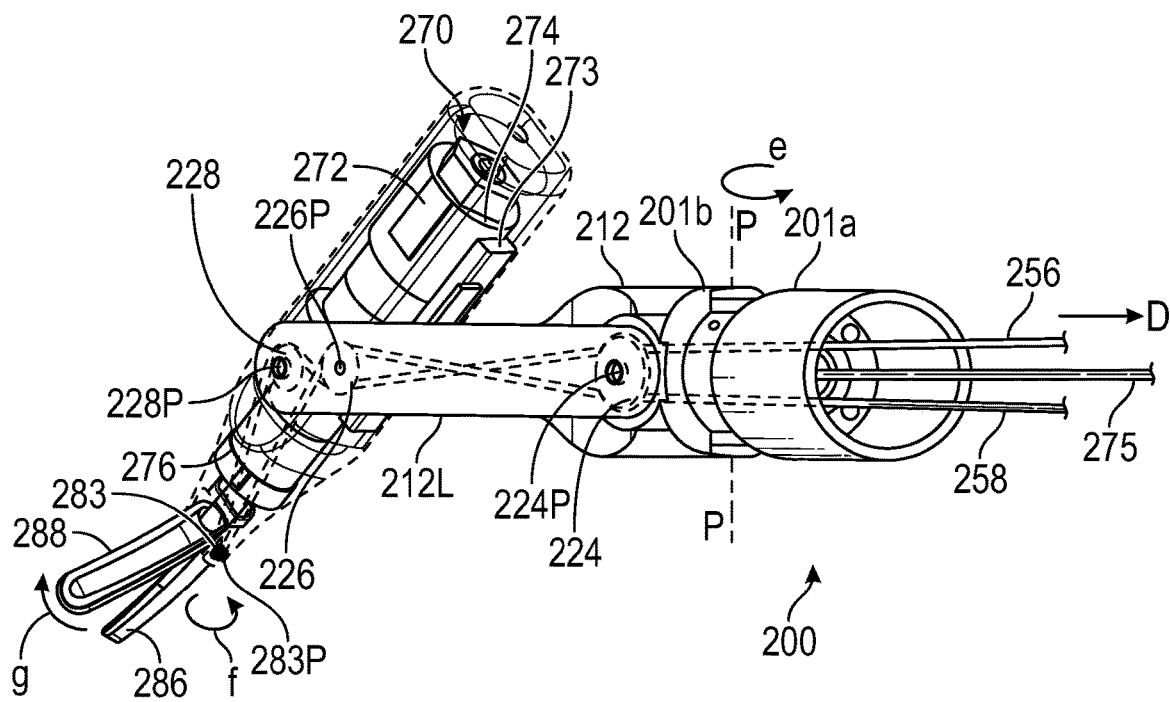
FIG. 4 is an enlarged, side, perspective view of a second side of the ultrasonic articulating end effector of FIG. 3 pivoted in the first direction.

Turning to FIGS. 3 and 4, articulating ultrasonic surgical end effector 200 includes an articulation assembly 201, a clevis 212 extending distally from the articulation assembly 201, and a transducer assembly 280 pivotable relative to the clevis 212. Transducer assembly 280 includes a transducer housing 282 including a shaft 284 extending distally from a body of transducer housing 282, an ultrasonic blade 286 extending distally from shaft 284, and a clamp arm 288 pivotable relative to shaft 284 and ultrasonic blade 286 via a clamp pulley 283 or other suitable mechanism.

Articulation assembly 201 operably couples end effector 200 to a surgical instrument or system. Articulation assembly 201 includes a proximal articulation link 201a and a distal articulation link 201b pivotable relative to the proximal articulation link 201a about a pivot axis "P" for achieving yaw articulation of the end effector 200. Proximal articulation link 201a is coupled to an elongated body portion 14 (FIG. 1) or an attaching device 1009, 1011 (FIG. 2) of a handheld or robotic system and distal articulation link 201b is operably coupled to clevis 212 of end effector 200. Articulation of distal articulation link 201b about pivot axis "P" effects corresponding articulation of clevis 212 extending therefrom in the same direction about pivot axis "P". As described below, a plurality of cables, for example, first cable 252, second cable 254, third cable 256, and fourth cable 258, extend through end effector 200 for manipulating end effector 200 and its components. Although articulation assembly 201 is described and illustrated as including a proximal articulation link 201a and a distal articulation link 201b, articulation assembly 201 may include only a single link or more than two links. Additionally, although end effector 200 is illustrated and described as including an articulation assembly 201, a proximal portion of end effector 200 (e.g., a proximal portion of clevis 212) may be coupled directly to a shaft of a surgical instrument or robotic arm without the inclusion of any articulation assembly such as articulation assembly 201.

Clevis 212 includes a pair of spaced-apart arms, in particular, right arm 212R (FIG. 3) and left arm 212L (FIG. 4) extending distally therefrom. Right arm 212R and left arm 212L are operably coupled to a portion of transducer assembly 280 (e.g., to shaft 284 via transducer housing 282) and pivotably secure transducer assembly 280 between right arm 212R and left arm 212L.

With reference to FIG. 3, a proximal portion of right arm 212R houses a pulley gear 220 which is rotatably coupled to right arm 212R via a pivot pin 220p and rotatable relative to right arm 212R. First cable 252 and second cable 254 extend distally through articulation assembly 201 (e.g., through channels defined through articulation assembly 201) and are routed around a pulley portion (not shown) of pulley gear 220 or operably coupled at their respective distal ends to the pulley portion of pulley gear 220. A distal portion of right arm 212R houses a distal gear 222 which is rotatably coupled to the distal portion of right arm 212R via a pivot pin 222p. Distal gear 222 is operably coupled to a gear portion (not shown) of pulley gear 220 via a belt 221 such that rotation of pulley gear 220 effects corresponding rotation of distal gear 222, though other coupling components may be used (e.g., geared, chain, etc.) for coupling pulley gear 220 to distal gear 222. Distal gear 222 is secured to shaft 284 (or another portion of transducer assembly 280) such that rotation of distal gear 222 effects rotation of shaft 284 relative to a longitudinal axis defined by clevis 212 to achieve pitch articulation.

According to the configuration described above, simultaneous proximal translation of first cable 252 and second cable 254 in the direction of arrow "A" pulls pulley gear 220 thereby urging distal articulation link 201b to rotate about pivot axis "P" in the direction of arrow "a" to achieve yaw articulation in one direction. Additionally, simultaneous proximal translation of first cable 252 and second cable 254 in the direction of arrow "A" may be met with distal translation or slack provided to third cable 256 and fourth cable 258 so as to not impart (or reduce) tension upon third cable 256 and fourth cable 258 when articulating in the direction of arrow "a". Proximal translation of only first cable 252 in the direction of arrow "A" (met with distal translation or slack provided to second cable 254) causes shaft 284 to pivot relative to clevis 212 in the direction of arrow "b" to achieve pitch articulation in one direction. Conversely, proximal translation of only second cable 254 in the direction of arrow "A" (met with distal translation or slack provided to first cable 252) causes shaft 284 to pivot relative to clevis 212 in the direction of arrow "c" to achieve pitch articulation in an opposite direction. Although described as two cables, first cable 252 and second cable 254 may be respective ends of a single cable.

Turning to FIG. 4, left arm 212L of clevis 212 houses a proximal pulley 224, a middle pulley 226, and a distal pulley 228. In particular, proximal pulley 224 is rotatably coupled to left arm 212L via a pivot pin 224p, middle pulley 226 is rotatably coupled to left arm 212L via a pivot pin 226p, and distal pulley 228 is rotatably coupled to left arm 212L via a pivot pin 228p. Third cable 256 extends distally through articulation assembly 201 (e.g., through channels defined through articulation assembly 201) and is routed about proximal pulley 224, routed about middle pulley 226, routed about distal pulley 228, and secured to clamp pulley 283. Similarly, fourth cable 258 extends distally through articulation assembly 201 (e.g., through channels defined through articulation assembly 201) and is routed about proximal pulley 224, routed about middle pulley 226, routed about distal pulley 228, and secured to clamp pulley 283. Although described as two cables, third cable 256 and fourth cable 258 may be respective ends of one single cable.

Clamp pulley 283 is engaged with clamp arm 288 and is rotatably coupled to the distal end of shaft 284 via a pivot pin 283p such that rotation of clamp pulley 283 in a first direction relative to shaft 284 pivots clamp arm 288 towards a clamping position, wherein clamp arm 288 is positioned adjacent ultrasonic blade 286 for clamping tissue therebetween, and such that rotation of clamp pulley 283 in a second, opposite direction relative to shaft 284 pivots clamp arm 288 towards an open positon, wherein clamp arm 288 is further-spaced from ultrasonic blade 286.

According to the configuration described above, simultaneous proximal translation of third cable 256 and fourth cable 258 in the direction of arrow "D" pulls middle pulley 226 and causes distal articulation link 201b to rotate about pivot axis "P" in the direction of arrow "e" to achieve yaw articulation in one direction (e.g., a direction opposite to that of arrow "a"). Additionally, simultaneous proximal translation of third cable 256 and fourth cable 258 in the direction of arrow "D" may be met with distal translation or slack provided to first cable 252 and second cable 254 (FIG. 3) so as to not impart (or to reduce) tension on first cable 252 and second cable 254 when articulating in the direction of arrow "e". Proximal translation of only third cable 256 in the direction of arrow "D" (met with distal translation or slack provided to fourth cable 258) causes clamp arm 288 to pivot relative to ultrasonic blade 286 in the direction of arrow "f" towards the clamping position. Conversely, proximal translation of only fourth cable 258 in the direction of arrow "D" (met with distal translation or slack provided to third cable 258) causes clamp arm 288 to pivot relative to ultrasonic blade 286 in the direction of arrow "g" towards the open position. Alternatively, third cable 256 and fourth cable 258 may be configured as a single cable secured about clamp pulley 283 and having its two ends extending proximally from clamp pulley 283, about distal pulley 228, middle pulley 226, and proximal pulley 224, proximally from clevis 212 and articulation assembly 201. In some aspects, a portion of fourth cable 258 and/or the pulley 283 may be disposed within transducer housing 282 to protect fourth cable 258 and pulley 283. As an alternative to third cable 256 and fourth cable 258 being operatively coupled to a clamp pulley 283, third cable 256 and fourth cable 258 may be coupled directly to clamp arm 288 on opposing sides of a pivot pin 283p to cause clamp arm 288 to pivot relative to ultrasonic blade 286.

Referring additionally to FIG. 1, with respect to use of end effector 200 with endoscopic surgical instrument 10, the proximal ends of first, second, third, and fourth cables 252, 254, 256, 258 of end effector 200 extend proximally through elongated body portion 12 to a suitable control mechanism configured to actuate cables or otherwise control articulation and clamping of the components of end effector 200. The proximal ends of first and second cables 252, 254 are operably coupled to second rotation knob 23 (or the drive component associated therewith) such that rotation of second rotation knob 23 in a first direction pivots transducer assembly 280 relative to clevis 212 in a first direction, and such that rotation of second rotation knob 23 in a second direction pivots transducer assembly 280 relative to clevis 212 in a second direction to achieve pitch articulation (e.g., in the direction of arrows "b" and "c" in FIG. 3). Such a configuration enables articulation of clamp arm 288 and ultrasonic blade 286 to a desired orientation relative to tissue to be treated. Additionally, with the proximal ends of first and second cables 252, 254 coupled to second rotation knob 23, proximal translation of second rotation knob 23 (e.g., pulling second rotation knob 23 away from handle assembly 12) urges distal articulation link 201b and clevis 212 to rotate about pivot axis "P" (e.g., in the direction of arrow "a") to achieve yaw articulation.

Proximal portions of third and fourth cables 256, 258 are operably coupled to clamp trigger 26 such that actuation of clamp trigger 26 from an un-actuated position to an actuated position pivots clamp arm 288 relative to ultrasonic blade 286 from the open position to the clamping position (e.g., in the direction of arrow "f"). Conversely, proximal portions of third and fourth cables 256, 258 are operably coupled to clamp trigger 26 such that return of clamp trigger 26 from the actuated position back to the un-actuated position pivots clamp arm 288 relative to ultrasonic blade 286 from the clamping position back to the open position (e.g., in the direction of arrow "g").

In addition to being coupled to clamp trigger 26, proximal portions of third and fourth cables 256, 258 may be operably coupled to first rotation knob 22 or other suitable component for controlling yaw articulation. For example, proximal portions of third and fourth cables 256, 258 may be routed through a pulley system (not shown) or otherwise operably routed through clamp trigger 26, with their respective proximal-most ends operably coupled to first rotation knob 22. Alternatively, proximal portions of third and fourth cables 256, 258 may be routed through a pulley system (not shown) or otherwise operably routed through first rotation knob 22, with their respective proximal-most ends operably coupled to clamp trigger 26. In either configuration, third and fourth cables 256, 258 are operably coupled to first rotation knob 22 or other mechanism such that proximal translation of first rotation knob 22 (e.g., urging first rotation knob 22 or other mechanism proximally toward second rotation knob 23) urges distal articulation link 201b and clevis 212 to rotate about pivot axis "P" (e.g., in the direction of arrow "e") to achieve yaw articulation in one direction.

Referring to FIGS. 2-4, with respect to use of end effector 200 with robotic surgical system 1000, the proximal ends of first, second, third, and fourth cables 252, 254, 256 258 of end effector 200 extend proximally through robot arm 1002 and each operably couple to a corresponding motor of control device 1004. Control device 1004 is operable, depending upon the input instructions received, to drive the appropriate motor thereof to pull the corresponding cable 252, 254, 256 258 to pivot transducer assembly 280 relative to clevis 212 in a desired direction to position clamp arm 288 and ultrasonic blade 286 to a desired orientation relative to tissue to be treated for achieving pitch articulation, to articulate end effector 200 about pivot axis "P" for achieving yaw articulation, to rotate, e.g., roll, end effector 200 about longitudinal axis "L," and to pivot clamp arm 288 between the open and clamping positions to clamp tissue between clamp arm 288 and ultrasonic blade 286.

Turning back to FIGS. 3 and 4, an inner assembly 270 of transducer assembly 280 is disposed partially within transducer housing 282, extends through shaft 284, and extends distally from shaft 284. Inner assembly 270 includes an ultrasonic transducer 272, which may be formed from a stack of piezoelectric transducer elements 273 or otherwise configured, an ultrasonic horn (not shown), and a waveguide 276. Electrodes 274 are interdisposed between piezoelectric transducer elements 273 are electrically coupled to a source of energy, e.g., via lead wires 275 extending through the pivots that couple transducer assembly 280 with clevis 212 and proximally through the instrument or system to a source of energy. Upon energization of electrodes 274, e.g., in response to activation of activation button 24 of surgical instrument (FIG. 1) or in response to an appropriate instruction provided by control device 1004 of robotic surgical system 1000 (FIG. 2), piezoelectric transducer elements 273 produce ultrasonic energy that is transmitted from ultrasonic transducer 272, to the ultrasonic horn, and along waveguide 276, which extends distally from transducer housing 282, to ultrasonic blade 286. Ultrasonic blade 286 extends distally from waveguide 276 and distally from shaft 284. Ultrasonic blade 286 is positioned adjacent clamp arm 288 to enable clamping of tissue between ultrasonic blade 286 and clamp arm 288 in the clamping position of clamp arm 288. Ultrasonic energy transmitted along waveguide 276 to ultrasonic blade 286 is communicated to tissue clamped between clamp arm 288 and ultrasonic blade 286 to treat tissue. Alternatively, clampless tissue treatment using just ultrasonic blade 286, e.g., via plunging, scoring, etc., may also be performed.

Figure 5:
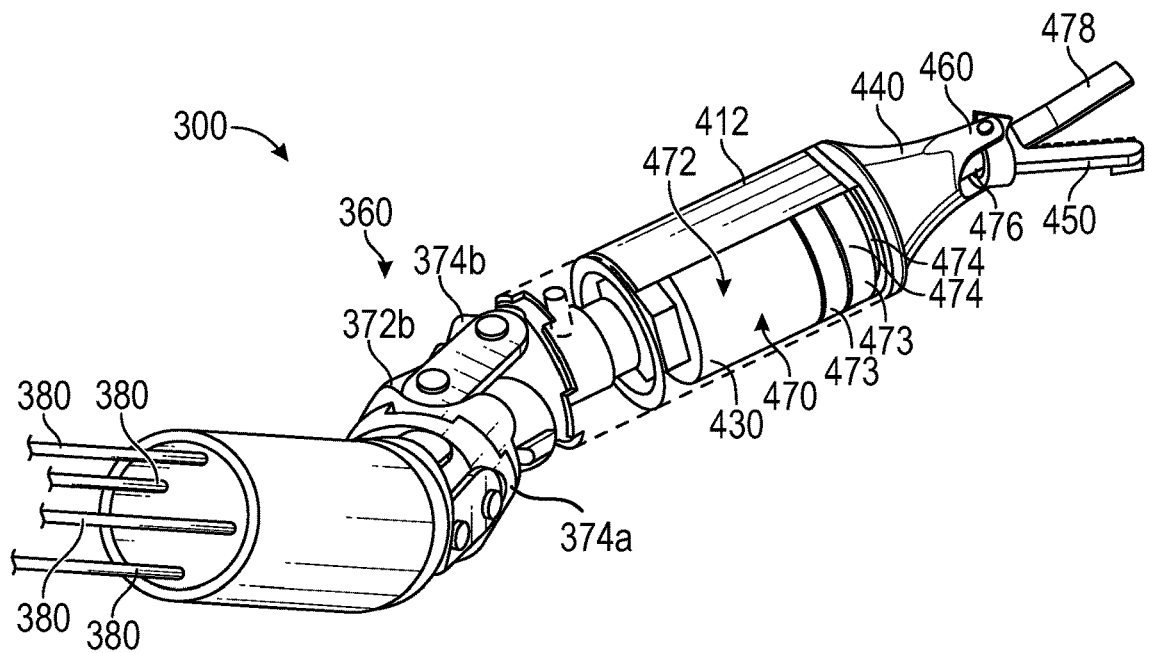
FIG. 5 is an enlarged, side, perspective view of another ultrasonic articulating end effector pivoted in a first direction in accordance with the present disclosure and configured for use with the endoscopic surgical instrument of FIG. 1, the robotic surgical system of FIG. 2, or any other suitable surgical instrument or system.
Figure 6:
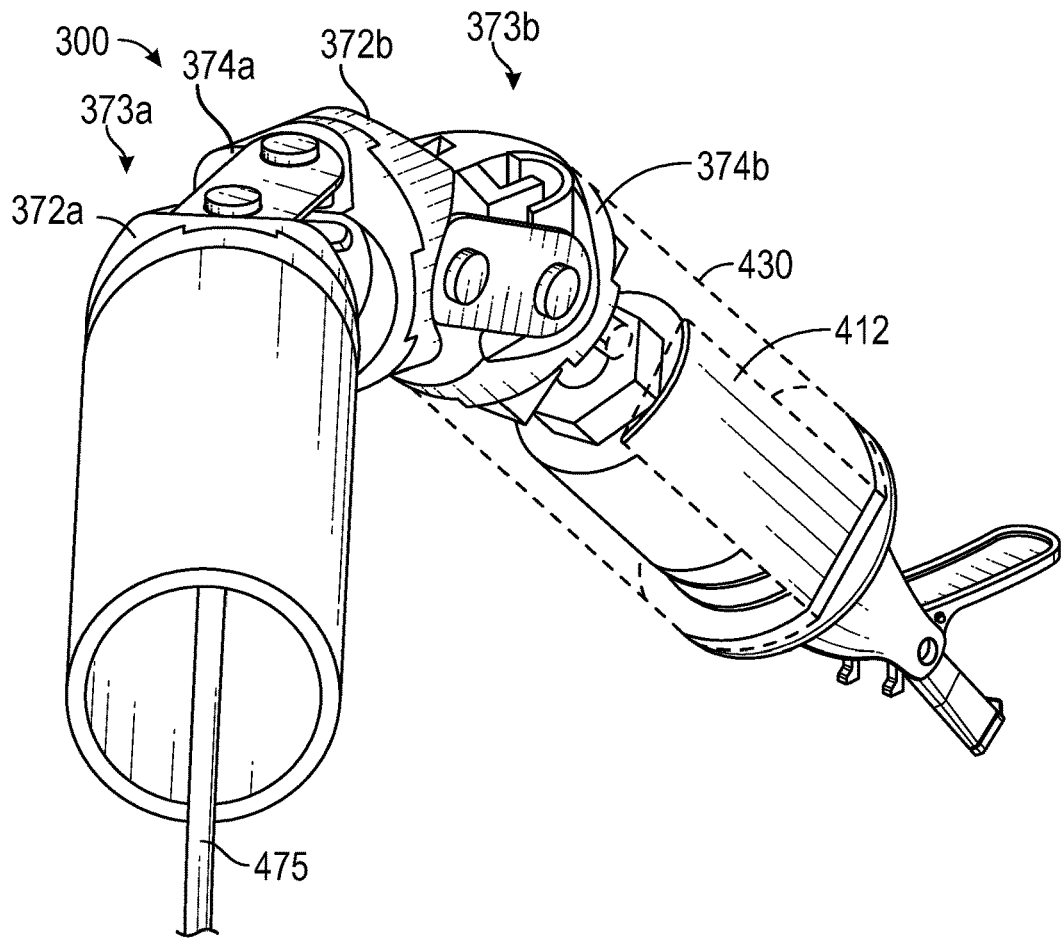
FIG. 6 is an enlarged, side, perspective view of the ultrasonic articulating end effector of FIG. 5 pivoted in a second direction.

Turning to FIGS. 5 and 6, another exemplary articulating ultrasonic surgical end effector is described. Articulating ultrasonic surgical end effector 300 includes an articulating section 360 that operably couples end effector 300 to a surgical instrument or system and articulates a distal end of the end effector 300 relative to a longitudinal axis of the instrument. For example, articulating section 360 may be defined at the distal end of elongated body portion 14 of endoscopic surgical instrument 10 (FIG. 1), at the distal end of attaching device 1009 of robot arm 1002 of robotic surgical system 1000 (FIG. 2), or at any other suitable location for enabling use of end effector 300 with a corresponding surgical instrument or system.

Articulating section 360 includes a plurality of intermediate articulating components, e.g., links, joints, etc., including a proximal articulating joint 373a, having a proximal link 372a and a distal link 374a, and a distal articulating joint 373b, having a proximal link 372b and a distal link 374b. The proximal link 372a of the proximal articulating joint 373a is rotatable (e.g., pivotable) relative to the distal link 374a of the proximal articulating joint 373a. Similarly, the proximal link 372b of the distal articulating joint 373b is rotatable (e.g., pivotable) relative to the distal link 374b of the distal articulating joint 373b. The distal link 374a of the proximal articulating joint 373a is fixedly coupled to the proximal link 372b of the distal articulating joint 373b. A plurality of articulation cables 380, e.g., four (4) articulation cables, or other suitable actuators, extend through articulating section 360 at different radial orientations.

In one aspect, articulation cables 380 are operably coupled to distal link 374b of distal articulation joint 373b at the distal ends thereof and extend proximally from the distal link 374b, through articulating section 360, and to an articulation sub-assembly (not shown), e.g., a gearbox assembly, actuator assembly, etc., to enable selective articulation of the distal link 374b of the distal articulating joint 373b (and, thus the distal end of end effector 300) relative to the proximal link 372a of proximal articulating joint 373a, e.g., about at least two axes of articulation (yaw and pitch articulation, for example).

Alternatively, one pair of articulation cables 380 may be operably coupled to a distal link 374b of distal articulating joint 373b while a second pair of articulation cables 380 is operably coupled to the distal link 374a of proximal articulating joint 373a. In this configuration, one pair of articulation cables 380 is operably coupled to the distal link 374b of distal articulating joint 373b at the distal ends thereof and extend proximally from the distal link 374b, through articulating section 360, and to an articulation sub-assembly (not shown), e.g., a gearbox assembly, actuator assembly, etc., to enable selective articulation of the distal link 374b (and, thus the distal end of end effector 300) relative to the proximal link 372b of the distal articulating joint 373b. The second pair of articulation cables 380 is operably coupled to a distal link 374a of proximal articulating joint 373a at the distal ends thereof and extend proximally from the distal link 374a, through articulating section 360, and to an articulation sub-assembly (not shown), e.g., a gearbox assembly, actuator assembly, etc., to enable selective articulation of the distal link 374a relative to the proximal link 372a of the proximal articulating joint 373a (and, thus the distal end of end effector 300). At least two of the links are oriented differently and/or differently configured to define different pivot axes, thereby enabling the articulation in at least two different directions. Articulation cables 380 are arranged to define a generally square configuration, although other suitable configurations are also contemplated.

With respect to articulation of the end effector 300 relative to the proximal link 372, actuation of articulation cables 380 is effected in pairs. More specifically, in order to pitch the end effector 300, the upper pair of articulation cables 380 is actuated in a similar manner while the lower pair of articulation cables 380 is actuated in a similar manner relative to one another but an opposite manner relative to the upper pair of articulation cables 380. With respect to yaw articulation, the right pair of articulation cables 380 is actuated in a similar manner while the left pair of articulation cables 380 is actuated in a similar manner relative to one another but an opposite manner relative to the right pair of articulation cables 380.

The distal link 374b of the distal articulating joint 373b is operably coupled to a proximal portion of the transducer housing 430 such that movement and articulation of the proximal articulating joint 373a and/or distal articulating joint 373b effects corresponding movement and articulation of the transducer housing 430.

End effector 300 further includes a shaft 440, forming a distal extension portion of transducer housing 430, a clamp arm 450 pivotable relative to shaft 440, a clamp pulley 460 operably coupled to clamp arm 450, and an inner assembly 470 disposed partially within transducer housing 430, extending through shaft 440, and extending distally from shaft 440. A proximal end of transducer housing 430 is fixedly mounted to a distal portion of articulating section 360 (e.g., at distal link 374). Shaft 440 includes two proximally extending arms 412 which couple the shaft 440 to the body of transducer housing 430.

Clamp pulley 460 is engaged with clamp arm 450 and rotatably coupled to the distal end of shaft 440 such that rotation of clamp pulley 460 in a first direction relative to shaft 440 pivots clamp arm 450 towards a clamping position, wherein clamp arm 450 is positioned adjacent ultrasonic blade 478 for clamping tissue therebetween, and such that rotation of clamp pulley 460 in a second, opposite direction relative to shaft 440 pivots clamp arm 450 towards an open positon, wherein clamp arm 450 is further-spaced from ultrasonic blade 478.

Figure 7:
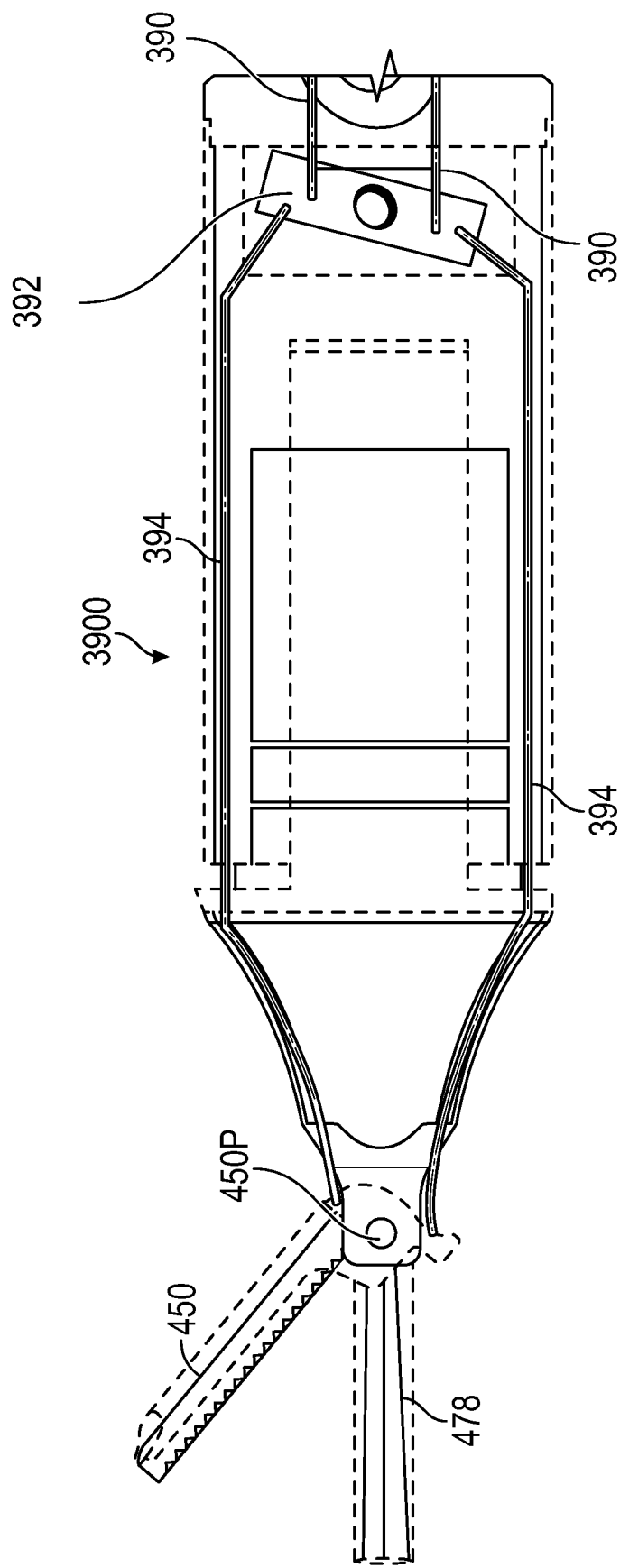
FIG. 7 is a side view of an exemplary drive mechanism usable with the end effector of FIG. 5.

In an aspect, clamp pulley 460 is operably coupled to one or more of articulating cables 380 such that actuation of one or more of articulating cables 380 effects rotation of clamp pulley 460 and in turn clamp arm 450. Alternatively, referring now to FIG. 7 a clamp drive mechanism 3900 including independent clamp drive cables 390 or a single drive rod (not shown) may extend through articulating section 360 to couple to, and control rotation of, a clamp lever 392 to pivot clamp arm 450 relative to ultrasonic blade 478. Such a configuration may use a camming mechanism to pivot clamp arm 450 relative to ultrasonic blade 478 between the open and clamping positions. In particular, distal ends of two drive cables 390 are coupled to the clamp lever 392 on opposite sides of a pivot point 392p to pivot the clamp lever 392 about the pivot point 392p via control of the drive cables 390. A pair of distal drive cables 394 extend distally from the clamp lever 392 to the clamp arm 450. In particular, proximal ends of the distal drive cables 394 are coupled to the clamp lever 392 and distal ends of the distal drive cables 394 are coupled to the clamp arm 450 on opposite sides of a pivot point 450p to control the pivoting of clamp arm 450 relative to the ultrasonic blade 478.

Referring to FIGS. 2, 5, and 6, with respect to use of end effector 300 with robotic surgical system 1000, the proximal ends of articulating cables 380 extend proximally through robot arm 1002 and each operably couple to a corresponding motor of control device 1004. Control device 1004 is operable, depending upon the input instructions received, to drive the appropriate motor thereof to pull the corresponding articulating cable 380 to articulate transducer housing 430 in a desired direction to position clamp arm 450 and ultrasonic blade 478 to a desired orientation relative to tissue to be treated, to pivot clamp arm 450 between the open and clamping positions to clamp tissue between clamp arm 450 and ultrasonic blade 478, and/or to rotate end effector 300 about its longitudinal axis.

Inner assembly 470 is disposed partially within transducer housing 430, extends through shaft 440, and extends distally from shaft 440. Inner assembly 470 includes an ultrasonic transducer 472, which may be formed from a stack of piezoelectric elements 473 or otherwise configured, an ultrasonic horn (not shown), and a waveguide 476. Electrodes 474 are interdisposed between piezoelectric transducer elements 473 and are electrically coupled to a source of energy, e.g., via lead wires 475 extending through the articulating section 360 and proximally through the instrument or system to the source of energy. Upon energization of electrodes 474, e.g., in response to activation of activation button 26 of surgical instrument (FIG. 1) or in response to an appropriate instruction provided by control device 1004 of robotic surgical system 1000 (FIG. 2), piezoelectric elements 473 produce ultrasonic energy that is transmitted from ultrasonic transducer 472, to the ultrasonic horn (not shown), and along waveguide 476, which extends distally from transducer housing 430, to ultrasonic blade 478. Ultrasonic blade 478 extends distally from waveguide 476 and distally from shaft 440. Ultrasonic blade 478 is positioned adjacent clamp arm 450 to enable clamping of tissue between ultrasonic blade 478 and clamp arm 450 in the clamping position of clamp arm 450. Ultrasonic energy transmitted along waveguide 476 to ultrasonic blade 478 is communicated to tissue clamped between clamp arm 450 and ultrasonic blade 478 to treat tissue. Alternatively, clampless tissue treatment using just ultrasonic blade 478, e.g., via plunging, scoring, etc., may also be performed.

Figure 8:
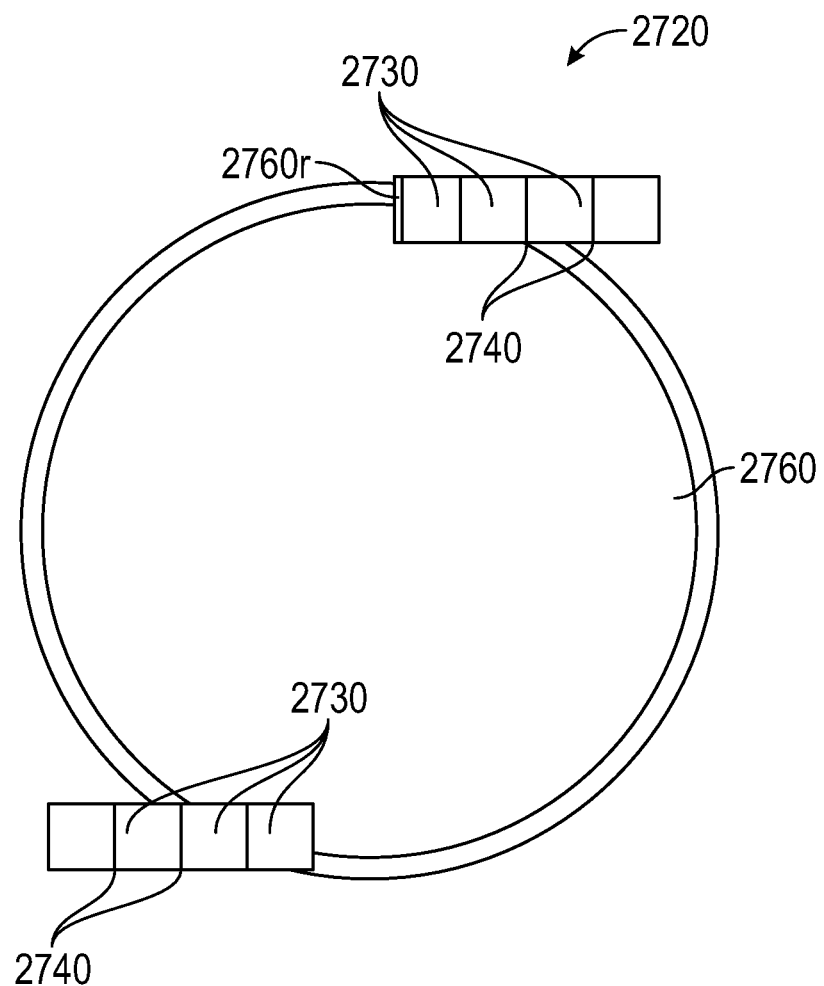
FIG. 8 is a cross-sectional view of a torsional ultrasonic transducer configured for use with the ultrasonic articulating end effector of FIG. 3 or 5, or any other suitable surgical instrument or system.

Turning now to FIG. 8, a cross-section view of another ultrasonic transducer usable with end effector 200 or end effector 300 is shown as a torsional ultrasonic transducer 2720. Torsional ultrasonic transducer 2720 may be disposed in transducer housing 282 of end effector 200 (FIGS. 3 and 4) or transducer housing 430 of end effector 300 (FIGS. 5 and 6), for example. Torsional ultrasonic transducer 2720 generates torsional ultrasonic vibrations in a circumferential direction of the piezoelectric transducer elements 2730 which are transmitted distally along the waveguide 2760 to the ultrasonic blade 286 (FIG. 3) or ultrasonic blade 478 (FIG. 5).

Each piezoelectric transducer element 2730 is operably coupled to an opposite side of waveguide 2760 to generate the torsional vibration in the circumferential direction of the piezoelectric transducer elements 2730. Any number of piezoelectric transducer elements 2730 may be utilized including a single or multiple stacked elements. In an aspect, each piezoelectric transducer element 2730 is disposed in a notch or recess 2760r defined by the waveguide 2760. Each lead wire 275 (FIG. 4) or lead wire 475 (FIG. 6) is coupled to a respective electrode 2740 which is coupled to respective piezoelectric transducer elements 2730 such that energizing of each electrode 2740 causes longitudinal vibration of the respective piezoelectric transducer elements 2730 and induces torsional vibration of the waveguide 2760 due to the positions being opposed to one another on opposite tangential sides of the waveguide 2760. These torsional ultrasonic vibrations are imparted to waveguide 2760 which, in turn, transmits the torsional ultrasonic vibrations along waveguide 2760 to ultrasonic blade 286 (FIG. 3) or ultrasonic blade 478 (FIG. 5) for treating tissue therewith. It is contemplated that use of a torsional ultrasonic transducer, e.g., torsional ultrasonic transducer 2720, may enable a reduction in the overall length of the transducer assembly, which may be advantageous in configurations where the transducer assembly is distally-positioned such as provided herein with respect to end effectors 200 (FIGS. 3 and 4) and 300 (FIGS. 5 and 6).

Figure 9:
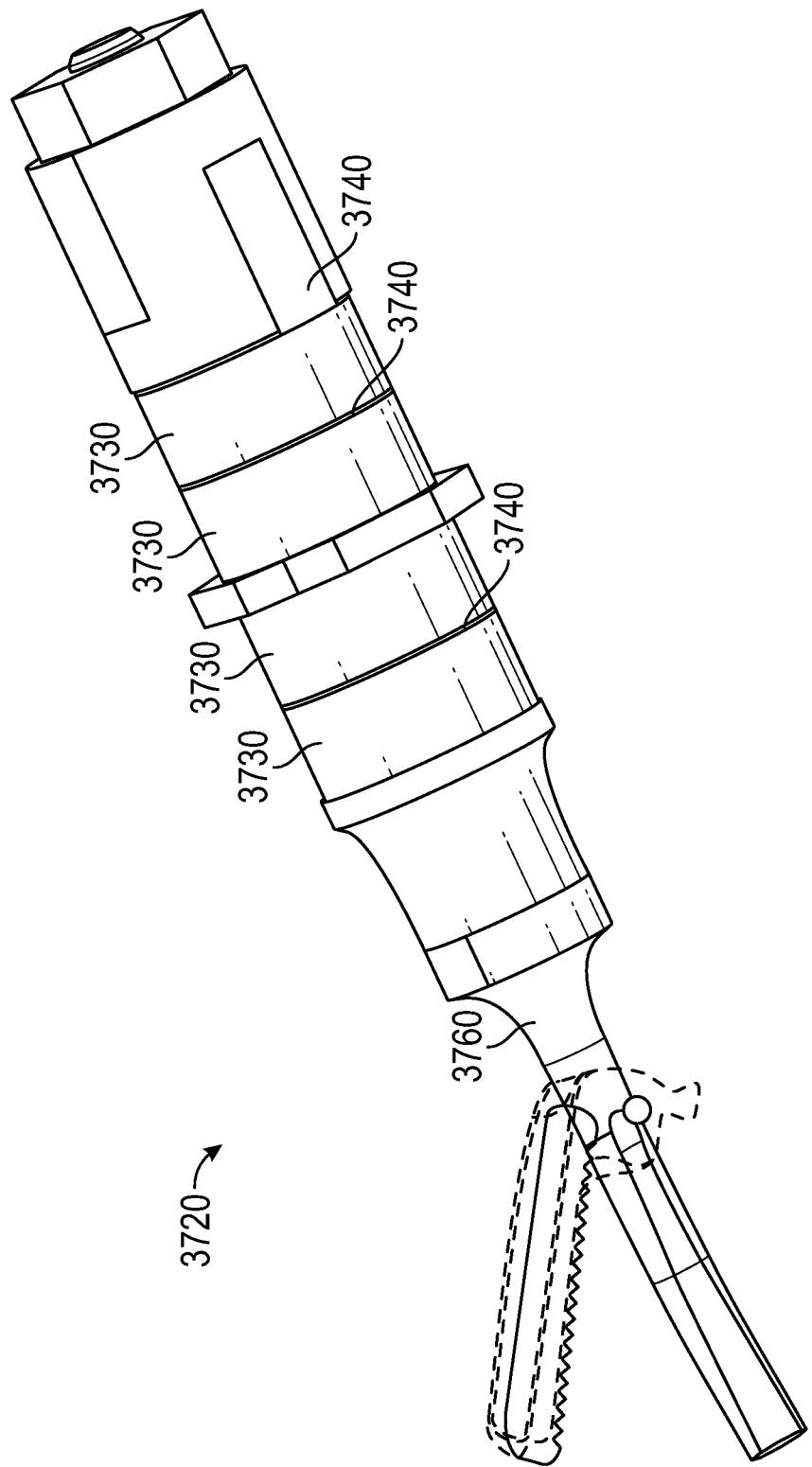
FIG. 9 is a side, perspective, view of another ultrasonic transducer configured for use with the ultrasonic articulating end effector of FIG. 3 or 5, or any other suitable surgical instrument or system.

Turning now to FIG. 9, a side, perspective view of another ultrasonic transducer usable with end effector 200 or end effector 300 is shown as a longitudinal ultrasonic transducer 3720. Longitudinal ultrasonic transducer 3720 may be disposed in transducer housing 282 of end effector 200 (FIGS. 3 and 4) or transducer housing 430 of end effector 300 (FIGS. 5 and 6), for example. Longitudinal ultrasonic transducer 3720 generates longitudinal ultrasonic vibrations in a longitudinal direction of the piezoelectric transducer elements 3730 which are transmitted distally along the waveguide 3760 to the ultrasonic blade 286 (FIG. 3) or ultrasonic blade 478 (FIG. 5).

Any number of piezoelectric transducer elements 3730 may be utilized including a single or multiple stacked elements. In an aspect, at least one electrode 3740 is disposed between adjacent piezoelectric transducer elements 3730. Each lead wire 275 (FIG. 4) or lead wire 475 (FIG. 6) is coupled to a respective electrode 3740 which is coupled to respective piezoelectric transducer elements 3730 such that energizing of each electrode 3740 causes longitudinal vibration of the respective piezoelectric transducer elements 3730 and induces longitudinal vibration of the waveguide 3760. These longitudinal ultrasonic vibrations are imparted to waveguide 3760 which, in turn, transmits the ultrasonic vibrations along waveguide 3760 to ultrasonic blade 286 (FIG. 3) or ultrasonic blade 478 (FIG. 5) for treating tissue therewith.

While several specific versions of devices in accordance with the present disclosure are shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

It should be understood that various features of the devices disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain features of devices in accordance with the present disclosure are described as being performed by a single module or unit for purposes of clarity, it should be understood that the techniques of this disclosure may be performed by a combination of units or modules associated with, for example, a medical device.

What is claimed is:

1. An articulating ultrasonic surgical end effector, comprising:
    an articulation assembly coupled to a distal end of an elongated body;
    a clevis operably coupled to the articulation assembly, the clevis articulable with respect to the elongated body via the articulation assembly; and
    a transducer assembly pivotably coupled to the clevis, the transducer assembly pivotable with respect to the clevis, the transducer assembly including:
        a transducer housing;
        an ultrasonic transducer disposed within the transducer housing;
        a waveguide disposed within the transducer housing, operably coupled to the ultrasonic transducer, and extending distally from the ultrasonic transducer;
        an ultrasonic blade disposed at a distal end of the waveguide and extending from the transducer housing, wherein ultrasonic energy produced by the ultrasonic transducer is transmitted along the waveguide to the ultrasonic blade for treating tissue; and
        a clamp arm pivotably coupled to the transducer housing and movable relative to the ultrasonic blade between an open position and a clamping position.

2. The articulating ultrasonic surgical end effector according to claim 1, wherein a pulley and cable arrangement operably couples the transducer assembly with the clevis to permit pivoting of the transducer assembly relative to the clevis.

3. The articulating ultrasonic surgical end effector according to claim 1, wherein a pulley and cable arrangement extends between the clamp arm and the clevis to permit pivoting of the clamp arm relative to the ultrasonic blade regardless of an articulated position of the transducer assembly relative to the clevis.

4. The articulating ultrasonic surgical end effector according to claim 1, further comprising:
    a pulley gear rotatably coupled to a proximal portion of the clevis;
    a distal gear rotatably coupled to a distal portion of the clevis and operably coupled to the transducer assembly such that rotation of the distal gear pivots the transducer assembly relative to the clevis; and
    a driver coupling the pulley gear to the distal gear.

5. The articulating ultrasonic surgical end effector according to claim 4, further comprising a first cable and a second cable operably coupled to the pulley gear, the first cable and the second cable configured to:
    rotate the pulley gear to cause the transducer assembly to pivot relative to the clevis when one of the first cable or the second cable is proximally actuated; and
    articulate a distal articulation link of the articulation assembly relative to a proximal articulation link of the articulation assembly when both of the first cable and the second cable are proximally actuated.

6. The articulating ultrasonic surgical end effector according to claim 1, wherein the ultrasonic transducer includes at least one piezoelectric element and at least one electrode.

7. The articulating ultrasonic surgical end effector according to claim 1, wherein the ultrasonic transducer defines a circular cross-sectional configuration.

8. The articulating ultrasonic surgical end effector according to claim 1, wherein a first notch and a second notch are defined along an outer surface of the ultrasonic transducer, on opposing sides thereof.

9. The articulating surgical end effector according to claim 8, wherein the ultrasonic transducer includes at least one piezoelectric element operably coupled to the first notch and at least one piezoelectric element operably coupled to the second notch, each of the piezoelectric elements configured to produce ultrasonic vibrations in a torsional direction.

10. A surgical system, comprising:
a robotic surgical system including a control device and a robotic arm; and
an articulating ultrasonic surgical end effector operably coupled to the robotic arm, the end effector comprising:
an articulation assembly coupled to a distal end of an elongated body;
a clevis operably coupled to the articulation assembly, the clevis articulable with respect to the elongated body via the articulation assembly; and
a transducer assembly pivotably coupled to the clevis, the transducer assembly pivotable with respect to the clevis, the transducer assembly including:
a transducer housing;
an ultrasonic transducer disposed within the transducer housing;
a waveguide disposed within the transducer housing, operably coupled to the ultrasonic transducer, and extending distally from the ultrasonic transducer;
an ultrasonic blade disposed at a distal end of the waveguide and extending from the transducer housing, wherein ultrasonic energy produced by the ultrasonic transducer is transmitted along the waveguide to the ultrasonic blade for treating tissue; and
a clamp arm pivotably coupled to the transducer housing and movable relative to the ultrasonic blade between an open position and a clamping position.

11. The surgical system according to claim 10, wherein a pulley and cable arrangement operably couples the transducer assembly with the clevis to permit pivoting of the transducer assembly relative to the clevis.

12. The surgical system according to claim 10, wherein a pulley and cable arrangement extends between the clamp arm and the clevis to permit pivoting of the clamp arm relative to the ultrasonic blade regardless of an articulated position of the transducer assembly relative to the clevis.

13. The surgical system according to claim 10, further comprising:
a pulley gear rotatably coupled to a proximal portion of the clevis, a distal gear rotatably coupled to a distal portion of the clevis and operably coupled to the transducer assembly such that rotation of the distal gear pivots the transducer assembly relative to the clevis, and a driver coupling the pulley gear to the distal gear.

14. The surgical system according to claim 13, further comprising a first cable and a second cable operably coupled to the pulley gear, the first cable and the second cable configured to:
rotate the pulley gear to cause the transducer assembly to pivot relative to the clevis when one of the first cable or the second cable is proximally actuated, and articulate a distal articulation link of the articulation assembly relative to a proximal articulation link of the articulation assembly when both of the first cable and the second cable are proximally actuated.

15. The surgical system according to claim 10, wherein the ultrasonic transducer includes at least one piezoelectric element and at least one electrode.

16. The surgical system according to claim 10, wherein the ultrasonic transducer defines a circular cross-sectional configuration.

17. The surgical system according to claim 10, wherein a first notch and a second notch are defined along an outer surface of the ultrasonic transducer, on opposing sides thereof.

18. The surgical system according to claim 17, wherein the ultrasonic transducer includes at least one piezoelectric element operably coupled to the first notch and at least one piezoelectric element operably coupled to the second notch, each of the piezoelectric elements configured to produce ultrasonic vibrations in a torsional direction.

19. An articulating ultrasonic surgical end effector, comprising:
an articulating section including a plurality of articulating links configured to enable articulation in at least two different planes; and
a transducer assembly extending distally from the articulating section, the transducer assembly articulable in the least two different planes via the articulating section, the transducer assembly including:
a transducer housing;
an ultrasonic transducer disposed within the transducer housing;
a waveguide disposed within the transducer housing, operably coupled to the ultrasonic transducer, and extending distally from the ultrasonic transducer;
an ultrasonic blade disposed at a distal end of the waveguide and extending from the transducer housing, wherein ultrasonic energy produced by the ultrasonic transducer is transmitted along the waveguide to the ultrasonic blade for treating tissue; and
a clamp arm pivotably coupled to the transducer housing and movable relative to the ultrasonic blade between an open position and a clamping position.

20. The articulating ultrasonic surgical end effector according to claim 19, further comprising a plurality of articulation cables operably coupled to at least one of the plurality of articulating links and configured to articulate the articulating section.

* * * * *